US012773517B2

(12) United States Patent
Giordano

(10) Patent No.: US 12,773,517 B2
(45) Date of Patent: Oct. 27, 2026

(54) SYSTEMS AND METHODS OF REDUCING STRESS WITH MUSIC

(71) Applicant: Matt Giordano, Conesus, NY (US)

(72) Inventor: Matt Giordano, Conesus, NY (US)

( * ) Notice: Subject to any disclaimer, the term of this patent is extended or adjusted under 35 U.S.C. 154(b) by 1324 days.

(21) Appl. No.: 17/575,836

(22) Filed: Jan. 14, 2022

(65) Prior Publication Data

US 2022/0218943 A1 Jul. 14, 2022

Related U.S. Application Data

(60) Provisional application No. 63/137,409, filed on Jan. 14, 2021.

(51) Int. Cl.

| | |
|---|---|
| ***A61M 21/02*** | (2006.01) |
| ***A61B 5/00*** | (2006.01) |
| ***A61B 5/024*** | (2006.01) |
| ***A61B 5/11*** | (2006.01) |
| ***A61B 5/16*** | (2006.01) |
| ***A61M 21/00*** | (2006.01) |
| ***G16H 20/70*** | (2018.01) |

(52) U.S. Cl.

CPC ............ *A61M 21/02* (2013.01); *A61B 5/024* (2013.01); *A61B 5/11* (2013.01); *A61B 5/165* (2013.01); *A61B 5/681* (2013.01); *A61B 5/7455* (2013.01); *G16H 20/70* (2018.01); *A61M 2021/0027* (2013.01)

(58) Field of Classification Search

CPC .......... A61M 21/02; A61M 2021/0027; A61M 2021/0022; A61M 2205/3569; A61M 2205/3592; A61M 2205/505; A61M 2209/088; A61M 2210/083; A61M 2230/06; A61M 2230/63; A61B 5/024; A61B 5/11; A61B 5/165; A61B 5/681; A61B 5/7455; G16H 20/70; G16H 40/63

USPC ........................................................ 600/26–28

See application file for complete search history.

(56) References Cited

U.S. PATENT DOCUMENTS

| | | | | |
|---|---|---|---|---|
| 2014/0141395 | A1 | 5/2014 | Gavish et al. | |
| 2014/0343354 | A1* | 11/2014 | Larson | A61M 21/02 600/28 |
| 2016/0346501 | A1* | 12/2016 | Hooper | A61B 5/4836 |
| 2017/0296429 | A1* | 10/2017 | Mayo | A61H 23/02 |
| 2018/0220901 | A1* | 8/2018 | LeBoeuf | A61B 5/7246 |
| 2019/0070057 | A1* | 3/2019 | Conner | A61H 23/02 |
| 2020/0147339 | A1* | 5/2020 | Mayo | A61M 21/02 |

(Continued)

*Primary Examiner* — Sunita Reddy

(74) *Attorney, Agent, or Firm* — Heslin Rothenberg Farley & Mesiti P.C.

(57) ABSTRACT

A method of reducing stress includes measuring an initial heart rate of a user of a stress reducing system. A target heart rate for the user is selected. A musical parameter of music is played at an initial musical parameter that is associated with the initial heart rate. The musical parameter is changed until the musical parameter matches a target musical parameter that is associated with the target heart rate. A current heart rate of the user is measured. If the current heart rate does not substantially match the target heart rate, the musical parameter is changed until the musical parameter substantially matches an intermediate musical parameter, the intermediate musical parameter associated with the current heart rate. Thereafter, the musical parameter is changed until the musical parameter substantially matches the target musical parameter.

5 Claims, 10 Drawing Sheets

(56) References Cited

U.S. PATENT DOCUMENTS

| | | | | |
|---|---|---|---|---|
| 2020/0243055 | A1 | 7/2020 | Grace | |
| 2021/0213239 | A1* | 7/2021 | Jones | A61H 23/0245 |
| 2022/0027123 | A1* | 1/2022 | Rando | A61B 5/024 |

* cited by examiner

To FIG. 11B

Graphical representation of an example of a "FEEL FEATURE" stress reduction technique HR = Heart Rate
bpm= Beats per Minute Graphical representation of an example of a "FEEL FEATURE" stress reduction technique HR= Heart Rate
HR= Beats per Minute

SYSTEMS AND METHODS OF REDUCING STRESS WITH MUSIC

CROSS-REFERENCE TO RELATED APPLICATIONS

This application is a non-provisional of, and claims the benefit of the filing date of, U.S. provisional application 63/137,409, filed Jan. 14, 2021, entitled, "SYSTEMS AND METHODS OF REDUCING STRESS WITH MUSIC," the contents of which are incorporated herein by reference.

TECHNICAL FIELD

The present disclosure relates to systems and methods of reducing stress. More specifically, the disclosure relates to systems and methods of detecting stress in a user and reducing that stress with the use of musical rhythms.

BACKGROUND

Practically everyone has experienced stress and anxiety. Such stress and anxiety can be caused by any number of external stimuli, including but not limited to, financial hardship, time pressure, emotional stress and the like.

Additionally, there are many people who suffer from ADHD (Attention Deficit Hyperactive Disorder), Tourette syndrome, Autism, as well as many other individuals with disabilities who are affected by sensory, focus, behavioral, emotional, organizational, social and anxiety issues. Various conditions, disorders, illnesses, or the like, tend to elevate the level of agitation and stress of the individual, sometimes with little external triggering.

Accordingly, there is a need for systems and methods that may help alleviate stress and anxiety in an individual. More specifically, there is a need for systems and methods that may help alleviate stress and anxiety in an individual through the use of music.

BRIEF DESCRIPTION

The present disclosure offers advantages and alternatives over the prior art by providing a stress reduction system worn by a user and a plurality of stress reduction methods for the user of the system. The stress reduction system includes a left-hand wrist device, a right-hand wrist device and a software application installed on a computerized device, such as a smart phone. The left-hand and right-hand wrist devices are in remote communication with the software application. The system may perform a plurality of stress reducing technique on the user. The system utilizes sensors which are operable to measure a variety of biological parameters, such as heart rate, hand movement and hand angle. The system is battery powered and is operable to communicate with the software application, such as via Bluetooth transmitter/receiver. The system can select which of a variety of senses (e.g., hands, sight and/or hearing) that are available by the user to participate in the stress reduction techniques. The system may also monitor hand movement and hand angle to simulate playing of a musical instrument during the performance of such stress reduction techniques.

A method of reducing stress in accordance with one or more aspects of the present disclosure includes measuring an initial heart rate of a user of a stress reducing system. A target heart rate for the user is selected, the target heart rate being different from the initial heart rate. The target heart rate being associated with a state of reduced stress of the user. Music is played to the user, wherein a musical parameter of the music is played at an initial musical parameter that is associated with the first initial heart rate. The musical parameter of the music is changed until the musical parameter substantially matches a target musical parameter that is associated with the target heart rate. A current heart rate of the user is measured once the musical parameter substantially matches the target musical parameter. The musical parameter of the music is changed, if the current heart rate is not within a predetermined acceptable range of the target heart rate, until the music's musical parameter substantially matches an intermediate musical parameter. The intermediate musical parameter being associated with the current heart rate. The musical parameter of the music is changed, once the musical parameter substantially matches the intermediate musical parameter, until the musical parameter substantially matches the target musical parameter.

Another method of reducing stress in accordance with one or more aspects of the present disclosure includes measuring an initial heart rate of a user of a stress reducing system. A first target heart rate for the user is selected, the first target heart rate being different from the initial heart rate. The first target heart rate being associated with a first state of reduced stress of the user. Music is played to the user, wherein a musical parameter of the music is played at an initial musical parameter that is associated with the initial heart rate. The musical parameter of the music is changed until the musical parameter substantially matches a first target musical parameter that is associated with the first target heart rate. The musical parameter is held at the first target musical parameter until the current heart rate of the user substantially matches the first target heart rate and the user has reached the first state of reduced stress.

Another method of reducing stress in accordance with one or more aspects of the present invention includes selecting a percussion instrument to play music for a user of a stress reducing system. One or more vibrators of the system play a first sequence of musical beats associated with playing the music with the percussion instrument. The first sequence of musical beats being felt by the user. The hands of the user are moved in an attempt to substantially match the first sequence of musical beats. Instruments of the system detect the movement of the hands. One or more vibrators of the system vibrate to simulate a feel to the user associated with playing the percussion instrument with the detected hand movement. The simulated feel to the user results in the user reaching a first state of reduced stress.

Another method of reducing stress in accordance with one or more aspects of the present disclosure includes selecting music for a user of a stress reducing system to hear. A percussion instrument is selected for the user to feel. The system plays an audio of the selected music. Instruments of the system detect the user's hand movements while the audio of the music is playing. One or more vibrators of the system vibrate to simulate a feel to the user associated with playing the percussion instrument with the detected hand movements. The simulated feel to the user results in the user reaching a first state of reduced stress.

A system for reducing stress of a user in accordance with one or more aspects of the present disclosure includes a first-hand wrist device, which includes a first user interface module (first UIM) connected to a first wrist strap. The first UIM includes a first vibrator operable to transmit controlled vibrations to the user's first wrist. The controlled vibrations of the first vibrator are operable to simulate a feel to the user associated with playing a first portion of a musical piece with a percussion instrument. The first wrist strap is configured to strap the first UIM to a user's first wrist. A second-hand wrist device includes a second user interface module (second UIM) connected to a second wrist strap. The second UIM includes a second vibrator operable to transmit controlled vibrations to the user's second wrist. The controlled vibrations of the second vibrator are operable to simulate a feel to the user associated with playing a second portion of the same music piece with the same percussion instrument. The second wrist strap is configured to strap the second UIM to a user's second wrist.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

DRAWINGS

The Disclosure Will be More Fully Understood from the Following Detailed Description Taken in Conjunction with the Accompanying Drawings, in which.

DETAILED DESCRIPTION

Certain examples will now be described to provide an overall understanding of the principles of the structure, function, manufacture, and use of the methods, systems, and devices disclosed herein. One or more examples are illustrated in the accompanying drawings. Those skilled in the art will understand that the methods, systems, and devices specifically described herein and illustrated in the accompanying drawings are non-limiting examples and that the scope of the present disclosure is defined solely by the claims. The features illustrated or described in connection with one example may be combined with the features of other examples. Such modifications and variations are intended to be included within the scope of the present disclosure.

The terms "significantly", "substantially", "approximately", "about", "relatively," or other such similar terms that may be used throughout this disclosure, including the claims, are used to describe and account for small fluctuations, such as due to variations in processing from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

System 100

A Stress Reducing System

Systems and methods of reducing stress are described in patent application publication no. US 2020/0341548 A1 to Matt Giordano, titled "SYSTEM, METHOD, AND APPARATUS FOR THERAPY AND COMPUTER USAGE", filed on Apr. 29, 2019, which is incorporated by reference herein in its entirety. Such stress reducing systems and methods may include certain body worn devices which are operable to detect an emotional state of a wearer/user of such a body-worn device by reading sensors associated with the body-worn device. Based upon data from the sensors and/or the emotional state detected, one or more of a plurality of sensation emitting devices of the body-worn device may be energized to provide a soothing sensation to the wearer (or user).

Figure 1:
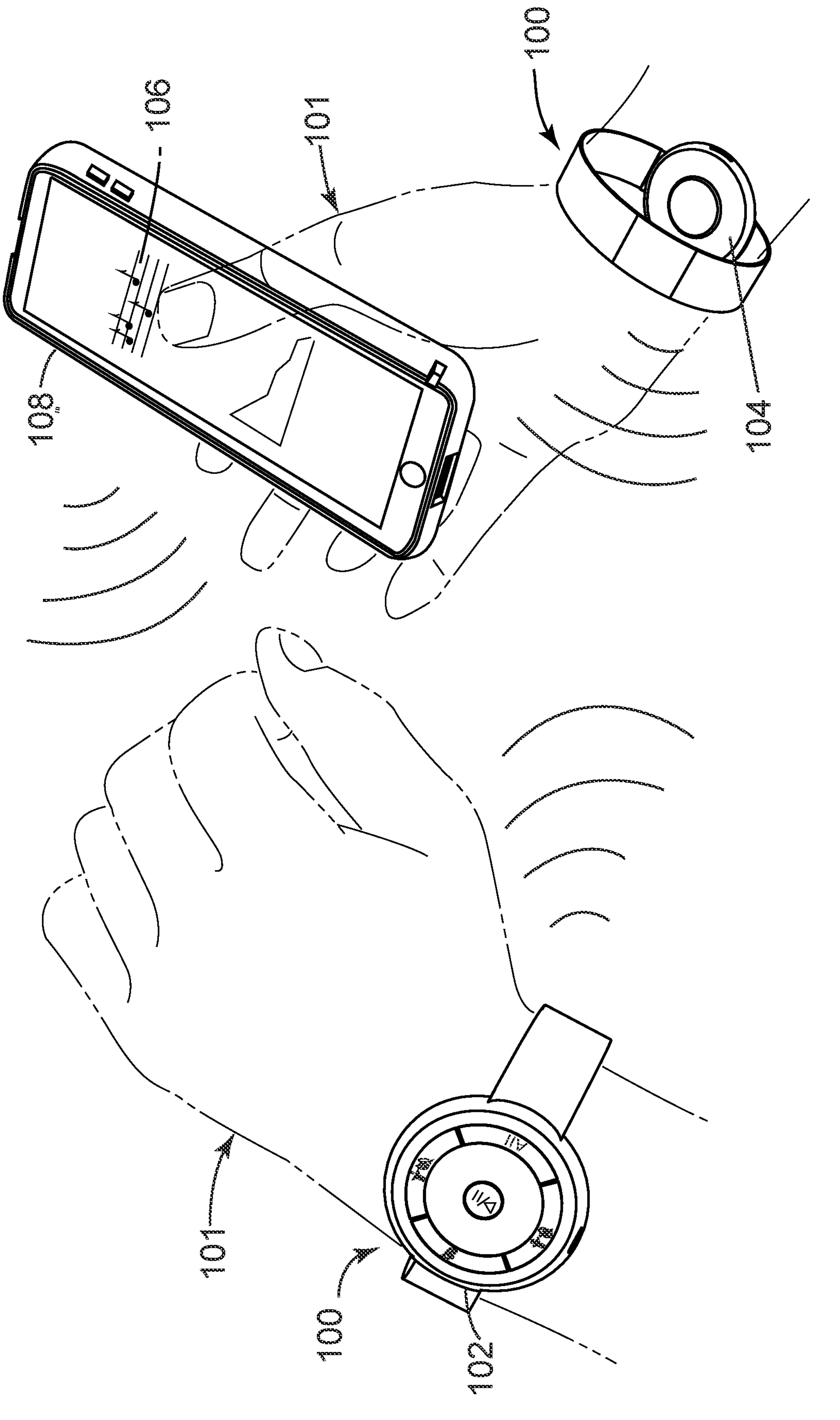
FIG. 1 depicts an example of a stress reducing system 100 for reducing stress of a wearer of the stress reducing system 100 according to aspects described herein.
Figure 2:
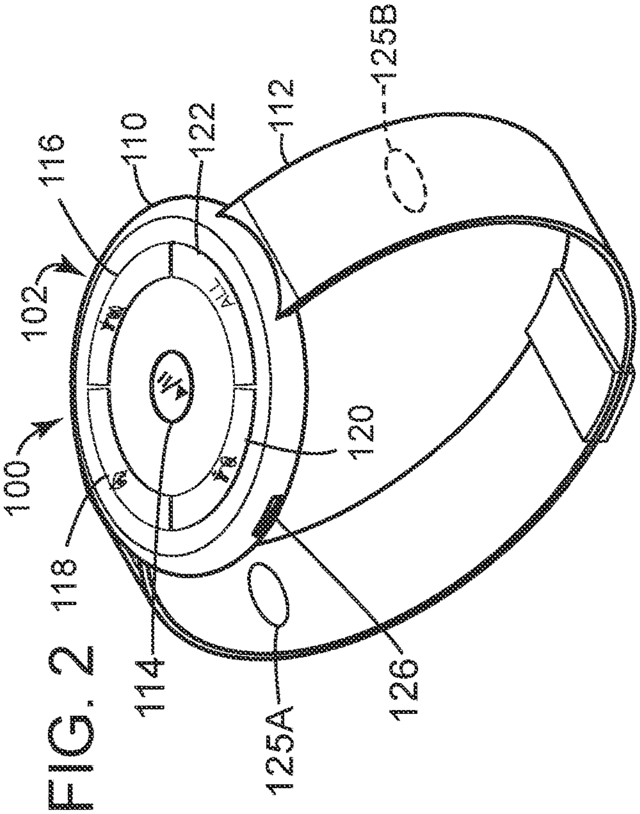
FIG. 2, depicts an example of a top perspective view of the left-hand wrist device of the stress reducing system of FIG. 1 in accordance with aspects described herein.
Figure 3:
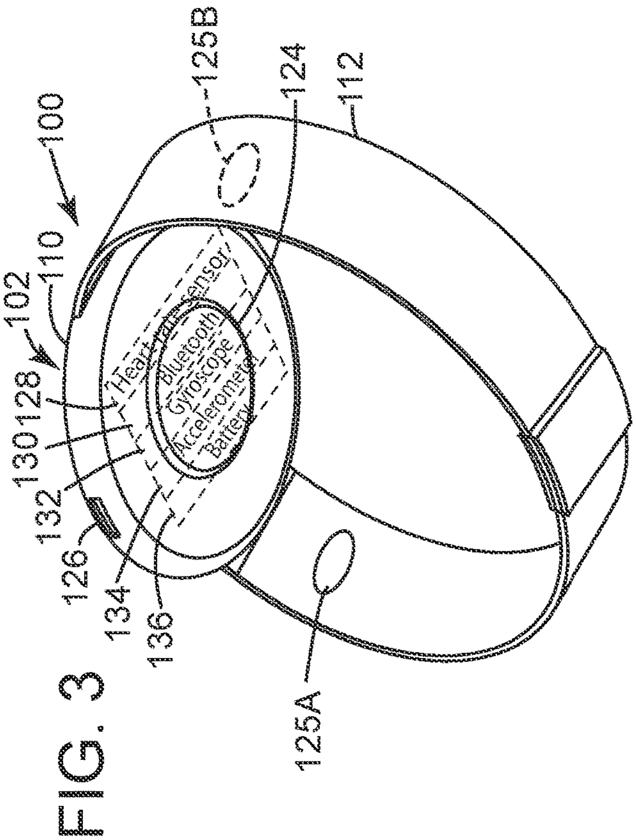
FIG. 3, depicts an example of a bottom perspective view of the left-hand wrist device of the stress reducing system of FIG. 1 in accordance with aspects described herein.
Figure 4:
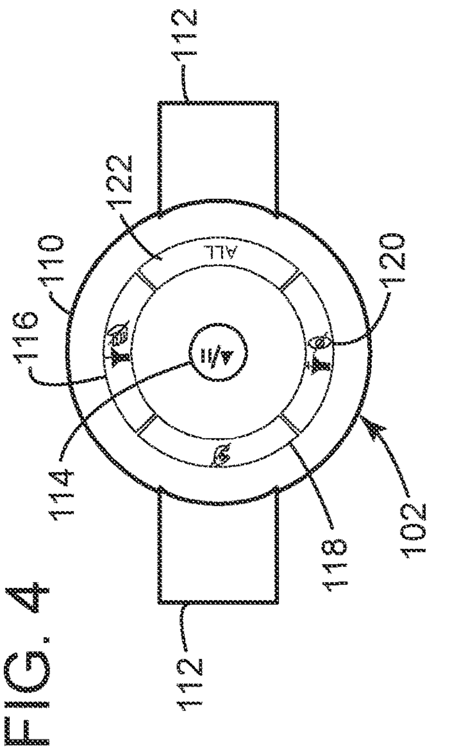
FIG. 4, depicts an example of a top view of the left-hand wrist device of the stress reducing system of FIG. 1 in accordance with aspects described herein.
Figure 5:
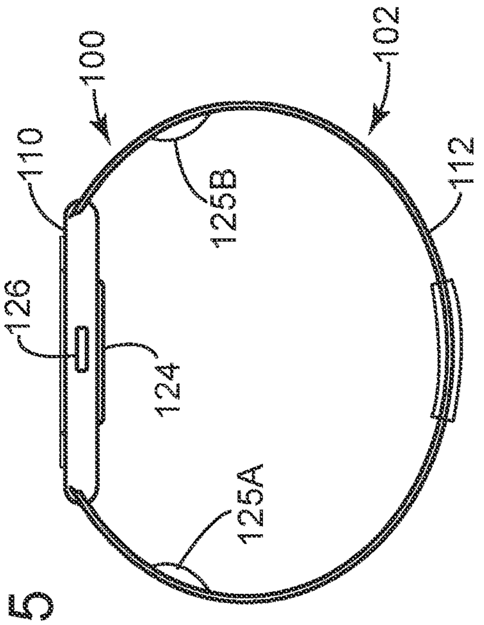
FIG. 5, depicts an example of a side view of the left-hand wrist device of the stress reducing system of FIG. 1 in accordance with aspects described herein.
Figure 7:
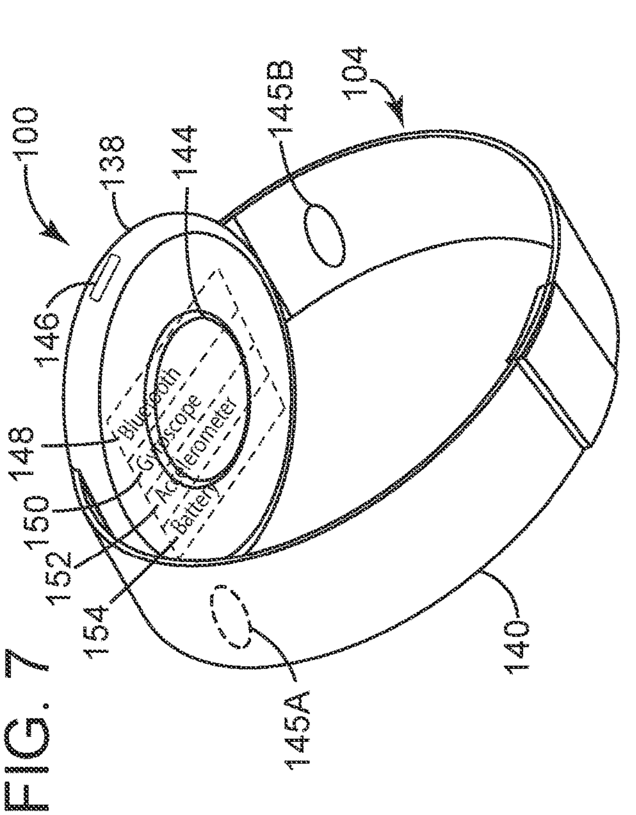
FIG. 7, depicts an example of a bottom perspective view of the right-hand wrist device of the stress reducing system of FIG. 1 in accordance with aspects described herein.
Figure 6:
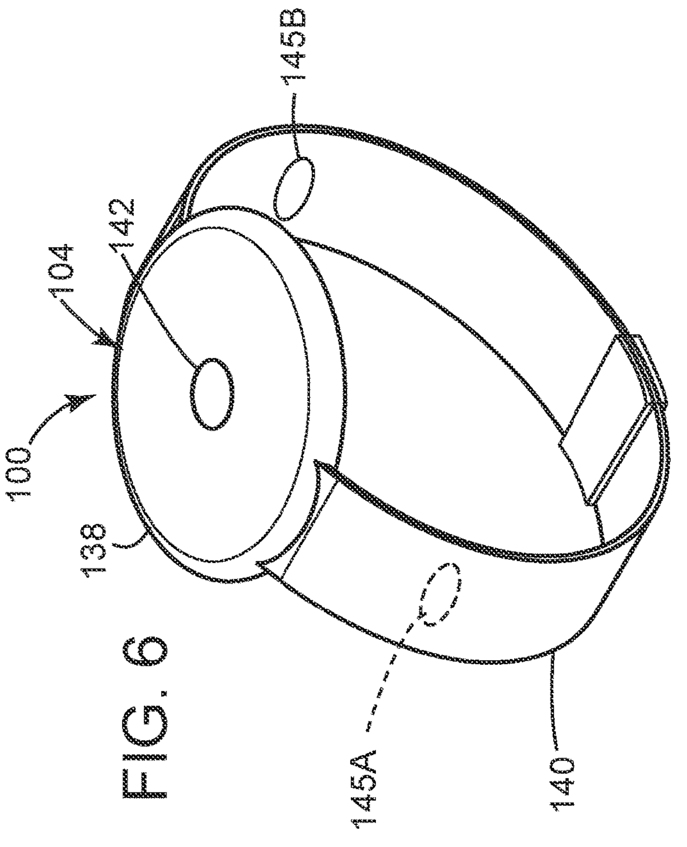
FIG. 6, depicts an example of a top perspective view of the right-hand wrist device of the stress reducing system of FIG. 1 in accordance with aspects described herein.
Figure 9:
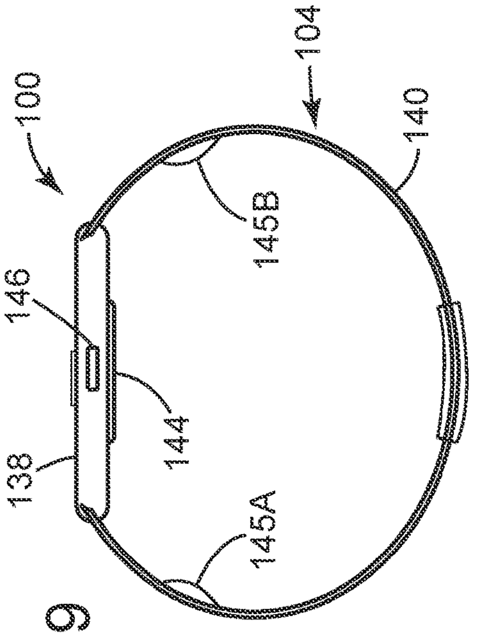
FIG. 9, depicts an example of a side view of the right-hand wrist device of the stress reducing system of FIG. 1 in accordance with aspects described herein.
Figure 8:
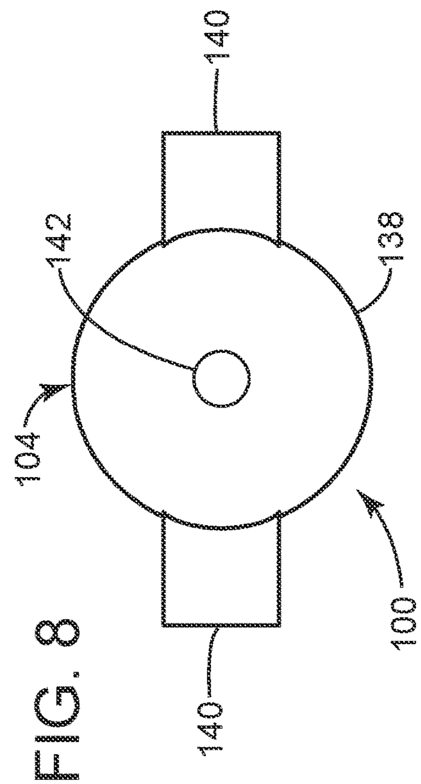
FIG. 8, depicts an example of a top view of the right-hand wrist device of the stress reducing system of FIG. 1 in accordance with aspects described herein.

Referring to FIG. 1, an example is depicted of a stress reducing system 100 for reducing stress of a wearer of the stress reducing system 100 in accordance with aspects described herein. The system 100 comprises a first-hand (for example the left hand) wrist device 102 and a second-hand (for example the right hand) wrist device 104 that are worn on the first (for example, left) and second (for example, right) wrists respectively of a user (or wearer) 101. For purposes herein, both the first-hand wrist device 102 and second-hand wrist device 104 are considered to be body-worn devices. Moreover, it is within the scope of this disclosure, that the first-hand and second-hand wrist devices 102, 104 may each be worn on either the right or left wrists of a user 101. As will be explained in greater detail herein, the first-hand and second-hand wrist devices 102, 104 are operable to communicate with a software application (App) 106 installed on a computerized device 108 (such as a smart phone, lap top computer or the like) to form the system 100, which alleviates stress and/or anxiety in a user. The first-hand and second-hand wrist devices 102, 104 are also operable to communicate with each other. Additionally, the software application (App) 106 may also be installed in one or both of the first-hand and second-hand wrist devices 102, 104. In the particular example illustrated in FIG. 1, the computerized device 102 is a smart phone. The system 100 is operable to measure certain biological parameters on the user that are related to stress and to control such musical parameters as tempo, volume, frequency and intensity of user selected music to help alleviate that stress.

The first-band wrist device 102 of the system 100 includes a first user interface module (first UIM) 110 connected to a first wrist strap 112 (see FIGS. 2-5). The first UIM 110 includes a first vibrator 124 that is operable to transmit controlled vibrations to the user's first wrist. The controlled vibrations of the first vibrator 124 are operable to simulate a feel to the user 101 associated with playing a first portion of a musical piece (such as musical beats of, a portion of, or all of a selected song) with a percussion instrument (such as a drum, conga or the like). The first wrist strap 112 of the system 100 is configured to strap the first UIM 110 to a user's first wrist. The first wrist strap 112 may also include one or more additional first wrist strap vibrators (see 125A and 125B of FIGS. 2, 3 and 5).

The second-hand wrist device 104 of the system 100 includes a second user interface module (second UIM) 138 connected to a second wrist strap 140 (see FIGS. 6-9). The second UIM 138 includes a second vibrator 144 that is operable to transmit controlled vibrations to the user's second wrist. The controlled vibrations of the second vibrator 144 are operable to simulate a feel to the user associated with playing a second portion of the same music piece with the same percussion instrument. So, for example, the second vibrator 144 may simulate the same portion of the same musical piece as vibrator 124, or a different portion of the same musical piece as vibrator 124. The second wrist strap 140 is configured to strap the second UIM 138 to a user's second wrist. The second wrist strap 140 may also include one or more additional second wrist strap vibrators (see 145A and 145B of FIGS. 6, 7 and 9).

Referring to FIGS. 2-5 an example is depicted of a top perspective view (FIG. 2), a bottom perspective view (FIG. 3), a top view (FIG. 4) and a side view (FIG. 5) of the first-hand wrist device 102 of system 100 in accordance with aspects described herein. The first-hand device 102 includes the first user interface module (UIM) 110, which is fastened to the user's first wrist (for example the left wrist) by the first wrist strap 112.

The first UIM 110 may include a center button 114 and four ring buttons 116, 118, 120 and 122 that are circumferentially positioned around the perimeter of the first UIM 110. The center button 114 may be operable to perform such functions as:

- a "Power on/off" function, which powers the first UIM on or off;
- a "Select" function, which selects music from the App 106;
- a "Play" function, which plays the selected music from the App 106;
- a "Pause" function, which pauses the selected music from the App 106; and
- a variety of other functions, such as turning various wrist device lights on and off.

Note that even though the above functions are illustrated as being mounted on the first UIM 110, the above functions may be mounted on and controlled by either the first UIM 110 or second UIM 138.

The ring button 116 may be operable to perform such functions as:

- a "Hands Occupied" function, which signals to the system 100 that the hands of the user are occupied and are not currently available to participate in any stress reduction techniques;
- a "Volume down" function, which decreases volume of music selected from the App 106; and
- an "Express" function or feature, which enables a certain stress reduction technique that will be explained in greater detail herein.

Note that even though the above functions are illustrated as being mounted on the first UIM 110, the above functions may be mounted on and controlled by either the first UIM 110 or second UIM 138.

The ring button 118 may be operable to perform such functions as:

- a "Hearing Occupied" function, which signals to the system 100 that the hearing of the user is occupied and is not currently available to participate in stress reduction techniques;
- a "Scroll Right" function, which signals to the App 106 to scroll a list of selectable music to the right in order to display other musical selections on the list to the user; and
- a "Feel" function or feature, which enables a certain stress reduction technique that will be explained in greater detail herein.

Note that even though the above functions are illustrated as being mounted on the first UIM 110, the above functions may be mounted on and controlled by either the first UIM 110 or second UIM 138.

The ring button 120 may be operable to perform such functions as:

- a "Sight Occupied" function, which signals to the system 100 that the sight of the user is occupied and is not currently available to participate in any stress reduction techniques;
- a "Volume up" function, which increases volume of music selected from the App 106; and
- a "Focus" function or feature, which enables a certain stress reduction technique that will be explained in greater detail herein.

Note that even though the above functions are illustrated as being mounted on the first UIM 110, the above functions may be mounted on and controlled by either the first UIM 110 or second UIM 138.

The ring button 122 may be operable to perform such functions as:

- an "All Senses Available" function, which signals to the system 100 that all senses of the user (e.g. hearing, hands/feeling and sight) are currently available to participate in stress reduction techniques; and
- a "Scroll Left" function, which signals to the App 106 to scroll a list of selectable music to the left in order to display other musical selections on the list to the user.

Note that even though the above functions are illustrated as being mounted on the first UIM 110, the above functions may be mounted on and controlled by either the first UIM 110 or second UIM 138.

The first UIM 110 also includes the first vibrator 124 which may be positioned on the underside of the first UIM 110. The first vibrator 124 is operable to transmit controlled vibrations (such as musical beats) to a user's wrist. A USB port 126 may be disposed on the side of the first UIM 110. The USB port 126 may be used for such functions as: charging the battery 136 of the first UIM 110 or transferring stored data from the first UIM 110 to the smart phone 108 or other computerized device.

Various sensors are located within the first user interface module 110 that may be used to measure and/or monitor certain biological parameters of the user 101 that are related to stress or that are used in techniques for alleviating stress. For example, the first UIM 110 may include a heart rate sensor 128 (for measuring the user's heart), such as a photoplethysmogram (PPG) sensor or an electrocardiography (ECG) sensor or the like. Note that the heart rate sensor 128 may be mounted on either the first UIM 110, the second UIM 138 or both.

The first UIM 110 may additionally include a first accelerometer 134 (for detecting a user's hand movements) and a first gyroscope 132 (for detecting an angle of a user's hands). The first accelerometer 134 and first gyroscope 132 are operable to detect various movements of the user's first hand. The first accelerometer 134 and first gyroscope 132 are in communication with the first vibrator 124 through the system 100 such that the first vibrator 124 is operable to simulate a feel to the user 101 associated with playing the percussion instrument with the detected movement of the user's first hand.

Note that other sensors used to measure other biological parameters may also be used and are within the scope of this invention.

Also positioned within the first UIM 110 may be a transmitter/receiver 130 (such as a Bluetooth type transmitter/receiver), which is operable to communicate with the App 106 of the smart phone 108, other computerized devices or the second UIM 138. Additionally, positioned within the first UIM 110 may be a rechargeable battery 136, which is operable to provide power to the first UIM 110.

The first wrist strap 112 of the first-hand wrist device 102 is connected to the first UIM 110 of the first-hand wrist device 102 and is operable to fasten to a user's first wrist. The first wrist strap 112 may include one or more first wrist strap vibrators 125A and 125B. The first wrist strap vibrators 125A, 125B, though illustrated as being two, may be any number. The first wrist strap vibrators 125A, 125B are operable to transmit controlled vibrations to the user's first wrist. The controlled vibrations of the one or more first wrist strap vibrators 125A, 125B may be operable to simulate a feel to the user associated with playing the first portion of the same music piece with the same percussion instrument that first vibrator 124 is playing. Alternatively, the first wrist strap vibrators 125A, 125B may be playing a different portion of the same musical piece that the first vibrator 124 is playing. It is also important to note, that each vibrator 124, 125A and 125B may operate independently of each other and may vibrate at different intensities, frequencies and/or frequency ranges.

Referring to FIGS. 6-9 an example is depicted of a top perspective view (FIG. 6), a bottom perspective view (FIG. 7), a top view (FIG. 8) and a side view (FIG. 9) of the second-hand (such as the right-hand) wrist device 104 of system 100 in accordance with aspects described herein. The second-hand device 104 includes the second user interface module (UIM) 138, which is fastened to a user's second wrist (such as the right wrist) by a second wrist strap 140.

The second UIM 138 communicates and cooperates with the first UIM 110 and the App 106 of the stress relieving system 100. Accordingly, the second UIM 138 may have less and/or different functionality and control features than that of the first UIM 110.

In the example illustrated in FIGS. 6-9, the second UIM 138 includes a center button 142, but may not include any ring buttons, such as the ring buttons 116, 118, 120 and 122 that are disposed on the first UIM 110. The center button 142 of the second UIM 138 is operable to power the second UIM 138 on or off but may not have any additional functionality.

The second UIM 138 may also include a second vibrator 144 positioned on the underside of the second UIM 138, which is operable to transmit controlled vibrations (such as musical beats) to a user's second wrist. The controlled vibrations of the second vibrator 144 are operable to simulate a feel to the user associated with playing a second portion of the same music piece with the same percussion instrument that the first vibrator 124 is playing. Accordingly, the second vibrator 144 may play the same portion, or a different portion, of the same musical piece that the first vibrator 124 is playing.

A USB port 146 may be disposed on the side of the second UIM 138. The USB port 146 may be used for such functions as: charging the battery 154 of the second UIM 138 or transferring stored data from the second UIM 138 to the smart phone 108 or other computerized device.

Various sensors are located within the second user interface module 138 that may be used to measure and/or monitor certain biological parameters of the user that are related to stress or that are used in techniques for alleviating stress. For example, the second UIM 138 may additionally include a second accelerometer 152 (for detecting a user's hand movements) and a second gyroscope 150 (for detecting an angle of a user's hands). The second accelerometer 152 and second gyroscope 150 are operable to detect various movements of the user's second hand. The second accelerometer 152 and second gyroscope 150 are in communication with the second vibrator 144 through the system 100 such that the second vibrator 144 is operable to simulate a feel to the user 101 associated with playing a percussion instrument with the detected movement of the user's second hand.

Note that other sensors used to measure other biological parameters may also be used and are within the scope of this invention.

Also positioned within the second UIM 138 is a transmitter/receiver 148 (such as a Bluetooth type transmitter/receiver), which is operable to communicate with the App 106 of the smart phone 108 or the first UIM 110. Additionally, positioned within the second UIM 138 is a rechargeable battery 154, which is operable to provide power to the second UIM 138.

The second wrist strap 140 of the second-hand wrist device 104 is connected to the second UIM 138 of the second-hand wrist device 104 and is operable to fasten to a user's second wrist. The second wrist strap 140 may include one or more second wrist strap vibrators 145A and 145B. The second wrist strap vibrators 145A, 145B, though illustrated as being two, may be any number. The second wrist strap vibrators 145A, 145B are operable to transmit controlled vibrations to the user's second wrist. The controlled vibrations of the one or more second wrist strap vibrators 145A, 145B may be operable to simulate a feel to the user associated with playing the second portion of the same music piece with the same percussion instrument that second vibrator 144 is playing. Alternatively, the second wrist strap vibrators 145A, 145B may be playing a different portion of the same musical piece that the second vibrator 144 is playing. It is also important to note, that each vibrator 144, 145A and 145B may operate independently of each other and may vibrate at different intensities, frequencies and/or frequency ranges.

During operation, the heart rate sensor 128 of the first-hand wrist device 102 will measure a user's heartbeat. Additionally, the accelerometers 134, 152 of the first-hand and second-hand wrist devices 102, 104 respectively will detect a user's hand movements. Additionally, the gyroscopes 132, 150 of the first-hand and second-hand wrist devices 102, 104 respectively will detect a user's hand angles. The data from these sensors 128, 132 134, 150, 152 may be used to detect and/or determine when the user is stressed from having a stressed heart rate and/or sporadic hand movements.

The first-hand and second-hand wrist devices 102, 104 may provide a stress alert to the user that the system 100 has detected stress through vibrations induced by one or more of the vibrators 124, 125A, 125B, 144, 145A or 145B. The system 100 may offer any number of reduction techniques or methods to alleviate that stress. Some of those stress reduction techniques are described herein named herein as: "Express Feature", "Focus Feature" and "Feel Feature", which will be explained in greater detail herein. These stress reduction techniques help a user manage stress, anxiety, focus challenges and sleep issues.

After receiving the stress alert, the user 101 can press the ring buttons 116, 118, 120, 122 on the first UIM 110 that represent which senses are currently being occupied by the user 101. Those senses are sight, hearing and hands (e.g., feeling). This will allow the stress reduction techniques to only function with their available senses. This allows the user to use this system and benefit from its stress reduction techniques anytime and anywhere, without these stress reduction techniques disrupting or distracting daily life activities of the user.

For example, the user 101 may be in a class watching and listening to the teacher giving a lecture, when the system 100 provides a stress alert. The user may then select the "Hearing Occupied" feature of ring button 118 and the "Sight Occupied" feature of ring button 120. This communicates to the system 100 that the user's hands are available and the user will only interact with the stress reduction techniques with the user's hands. The accelerometers 134, 152 and gyroscopes 132, 150 will detect hand movements and the angle of the user's hands. The App 106 will simulate to the user 101 the playing of percussion sounds when the user waves or moves the user's hands, or when the user taps on a table or a lap. The user 101 will feel the vibrations associated with the percussions sounds through the vibrators 124, 125A-B, 144 and 145A-B of the first-hand and second-hand wrist straps 102, 104.

The vibrators 124, 125A-B, 144A and 145A-B are embedded in each first-hand and second-hand wrist devices 102, 104 respectively, enabling the user to feel the drumming and the music. This makes it a more realistic and effective experience. The heart rate sensor 128 allows the stress reduction techniques to adapt and adjust the stress reduction techniques in real time to the user's stress levels so the end results will be even more accommodating and effective for the user 101.

A discussion of various stress reduction techniques that may be used with the system 100 follows:

Express Feature

A First Example Stress Reduction Technique

As an overview, the purpose of the "Express Feature" stress reduction technique is to enable the user 101 to creatively jam along to selected music to either help pull the user up into a more upbeat state if the user is feeling sluggish or to help pull the user down into a more calm and relaxed state if the user is feeling upset or anxious. The user 101 may pick a song on, for example, the App 106 and then a percussion instrument in, for example, the App 106, to play along to the selected music.

The accelerometers 134, 152 and the gyroscopes 132, 150 in the first-hand and second-hand wrist devices 102, 104 respectively of system 100 will detect when the user 101 is moving the user's hands to create the simulated percussion sounds. The user 101 will feel the user's playing from one or more of the vibrators 124, 125A-B, 144, 145A-B in the wrist devices 102, 104 for a more realistic and effective jam experience. Another of the one or more vibrators 124, 125A-B, 144, 145A-B may vibrate as a metronome to help keep the user 101 playing to the right speed/tempo of the music or, more specifically, to the beats per minute (BPM) of the music.

The song may start with a musical parameter, such as tempo, volume, intensity or frequency that is associated with a user's heart rate. If the user desires to be more calm and relaxed, the song will gradually slow down the musical parameter, such as its tempo (e.g., the music's BPM) and/or gradually lower the volume of the music until the music reaches a target musical parameter that is associated with a target heart rate of the user. This will help to pull the user down into a more calm and relaxed state. When the musical parameter (e.g. tempo) has reached the target musical parameter associated with the users target heart rate, the system 100 will detect the users current heart rate. If the user's heart rate does not substantially match the target heart rate (e.g., is not within an acceptable predetermined range of the target heart rate), the music's musical parameter (such as, tempo and/or volume) will gradually rise to an intermediate target musical parameter that is associated with the users current heart rate. The music' musical parameter will then continue reducing the same way it did in the previous cycle. This cycle may repeat if the user doesn't reach the user's target heart rate.

If the user needs an uplifting, upbeat experience, this entire process will go in the exact opposite direction. For example, the users initial heart rate (e.g., BPM) may be slow. In that case, the system 100 will select a target heart rate that is higher than the initial heart rate of the user. The system will then function to increase the user's heart rate instead of decreasing it.

Figure 10:
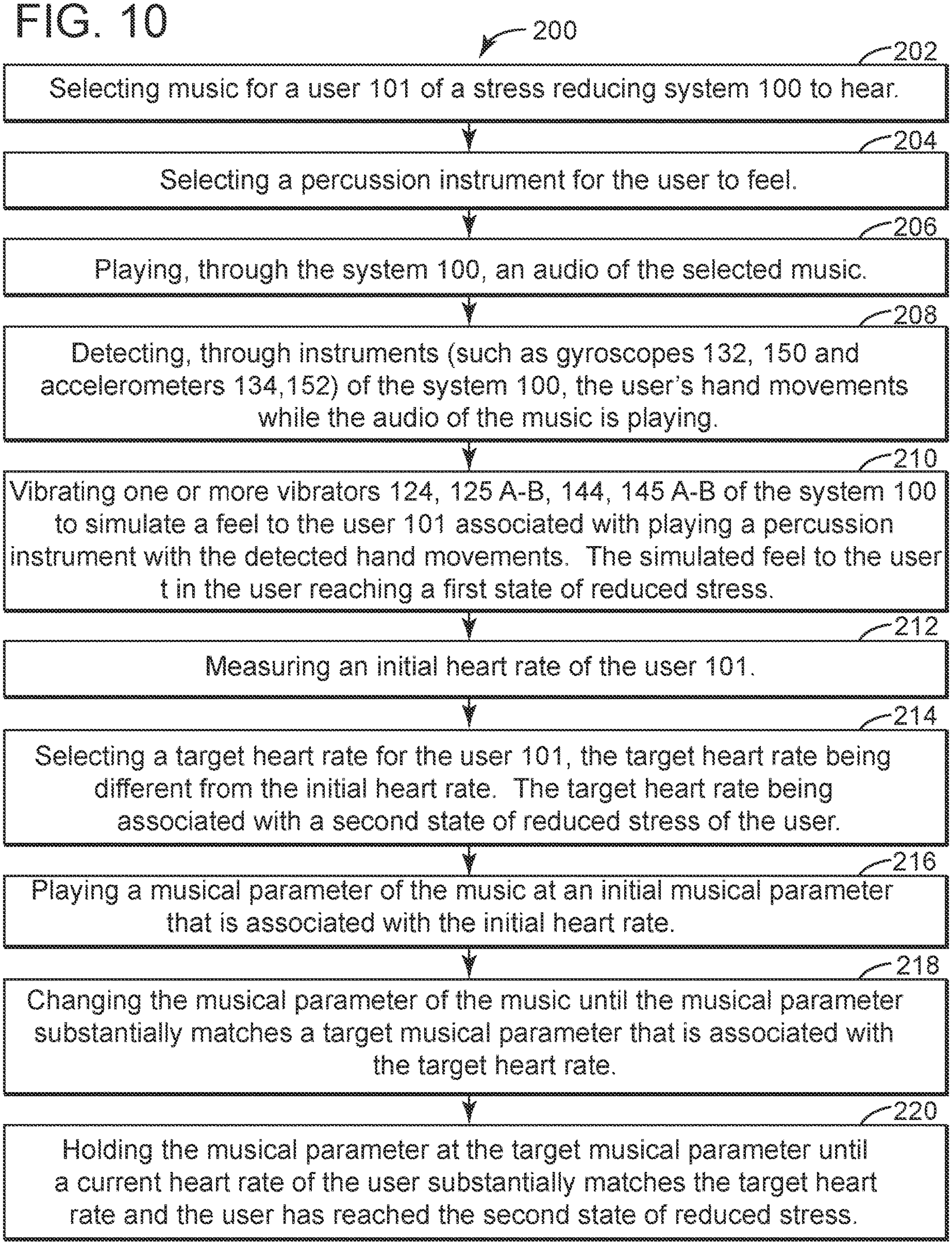
FIG. 10, depicts an example of a flow diagram of a method of reducing stress by a user of a stress reducing system, in accordance with aspects described herein.

Referring more specifically to FIG. 10, an example is depicted of a flow diagram 200 of a method of reducing stress by a user of a stress reducing system 100, in accordance with aspects described herein. The flow diagram 200 depicts examples of the method colloquially named the Express Feature method.

The method 200 starts at 202, wherein music is selected for a user 101 of a stress reducing system 100 to hear. The music may be selected by the user 101 or may be selected by the software on the App. 106. The music may be a song preferred by the user.

At 204, a percussion instrument is selected for the user 101 to feel. The percussion instrument may be selected, for example, by the user from a selection of percussion instruments on the App. 106. The percussion instrument may be, for example, drums, bongos, castanets, conga, tambourine, or other types of percussion instruments.

At 206, the system 100 then plays an audio of the selected music for the user to hear.

At 208, instruments (such as gyroscopes 132, 150 and accelerometers 134, 152) of the system 100 will detect the user's hand movements while the audio of the music is playing.

At 210, one or more vibrators 124, 125A-B, 144, 145A-B of the system 100 will provide vibrations to simulate a feel to the user 101, which is associated with playing the selected percussion instrument with the hand movements that were detected by the instruments of the system. The simulated feel to the user results in the user reaching a first state of reduced stress.

At 212, the heart rate sensor 128 of the system 100 may measure an initial heart rate of the user 101.

At 214, the system 101 may select a target heart rate for the user 101. The target heart rate being different from the initial heart rate. The target heart rate being associated with a second state of reduced stress of the user.

At 216, a musical parameter of the music is played at an initial musical parameter that is associated with the first initial heart rate. The musical parameter may be, for example, volume or tempo if the music is being played as an audio through an audio feature of the system. The musical parameter may also be, for example, frequency or intensity of vibrations if the music is being played through the various vibrators 124, 125A-B, 144, 145A-B of the system 100.

At 218, the musical parameter of the music may be changed until the musical parameter substantially matches a target musical parameter that is associated with the target heart rate.

At 220, the musical parameter may be held at the target musical parameter until a current heart rate (as measured by the heart rate sensor 128 of the system 100) of the user 101 substantially matches the target heart rate and the user has reached the second state of reduced stress.

For purposes of clarity, substantially matching the target heart rate, shall mean being within an acceptable predetermined range of the target heart rate. So, for example, the acceptable range may be within 6 beats per minute (BPM), within 5 BPM, or within 3 BPM of the target heart rate.

Focus Feature

A Second Example Stress Reduction Technique

As an overview, in the Focus Feature stress reduction technique, a user may select music from the App 106 or other device. The music will play a percussion instrument, such as for example a conga, in a certain sequence of beats that goes along with the music. The user may feel the high conga sounds from the vibrators 124, 125A-B in the first-hand wrist device 102 and may feel the low conga sounds from the vibrators 144, 145A-B in the second-hand wrist device 104. (Note that this may be reversed in that the high conga sounds may emanate from the vibrators 144, 145A-B of the second-hand wrist device 104 and the low conga sounds may emanate from the vibrators 124, 125A-B of the first-hand wrist device 102).

The user will then play back the same sequence of beats with the same hand sequence. For example, the system may play the conga as the Right hand, Left hand, Right hand, and then Right hand. Then the user will play it back the same way. The user may hear the drumming from the conga or other percussions instruments being played and may feel the conga playing from the vibrators 124, 125A-B, 144, 145A-B in the wrist devices 102, 104.

If the user plays the correct hand sequence, then the hand rhythm or beat sequence may get more complicated. If the user does not play it correctly, the hand rhythm or beat sequence may stay at the same level of difficulty or may stay exactly the same. The purpose of this Focus Feature is to help the user focus the user's attention by engaging working memory via rhythm and music, and therefore achieve a more relaxed state.

Figure 11A:
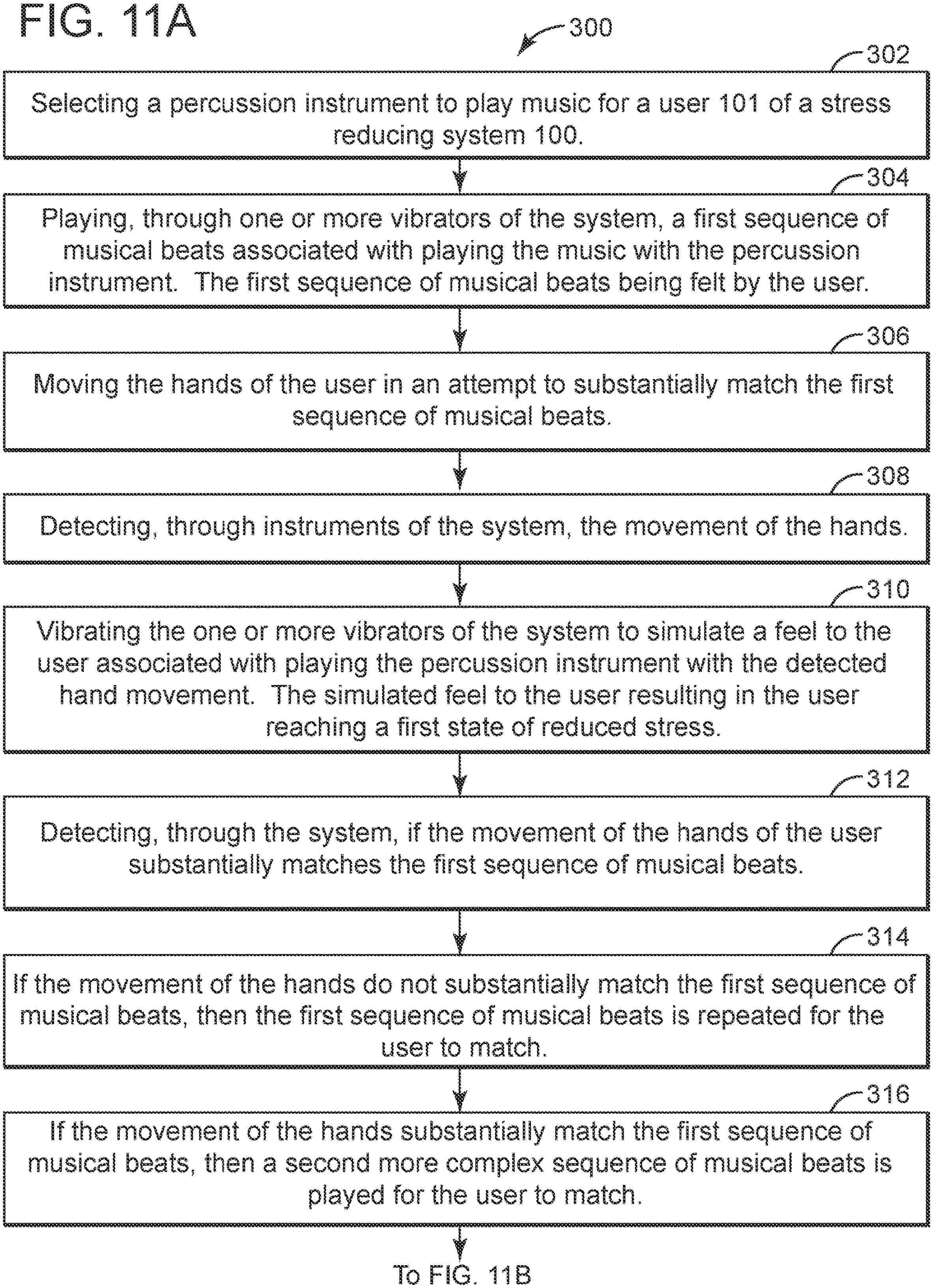
FIG. 11A, depicts another example of a first part of a flow diagram of a method of reducing stress by a user of a stress reducing system, in accordance with aspects described herein.

Referring more specifically to FIG. 11A, an example is depicted of a first part of a flow diagram 300 of a method of reducing stress by a user of a stress reducing system 100, in accordance with aspects described herein. The flow diagram 300 depicts examples of the method colloquially named the Focus Feature method.

The method 300 starts at 302, wherein a percussion instrument is selected to play music for a user 101 of a stress reducing system 100.

At 304, one or more of the vibrators 124, 125A-B, 144, 145A-B of the system 100 vibrate (or play) a first sequence of musical beats associated with playing the music with the selected percussion instrument. The first sequence of musical beats is felt by the user 101.

Optionally, an audio version of the musical beats and/or an audio of a musical piece related to the musical beats, may be selected to play while the sequence of musical beats are being played by the vibrators.

At 306, the hands of the user are moved in an attempt to substantially match the first sequence of musical beats.

At 308, instruments (such as accelerometers 134, 152 and gyroscopes 132, 150) of the system 100 detect the movement of the hands.

At 310, the vibrators 124, 125A-B, 144, 145A-B of the system 100 vibrate to simulate a feel to the user 101 associated with playing the selected percussion instrument with the detected hand movement. The simulated feel to the user results in the user reaching a first state of reduced stress.

At 312, the system detects if the movement of the hands of the user substantially match the first sequence of musical beats.

At 314, if the movement of the hands do not substantially match the first sequence of musical beats, then the first sequence of musical beats is repeated for the user to try to match. Alternatively, the vibrators may play another sequence of musical beats, which are no more complex than that of the first sequence of musical beats for the user to try to match.

At 316, if the movement of the hands substantially match the first sequence of musical beats, then a second more complex sequence of musical beats is played for the user to match.

Figure 11B:
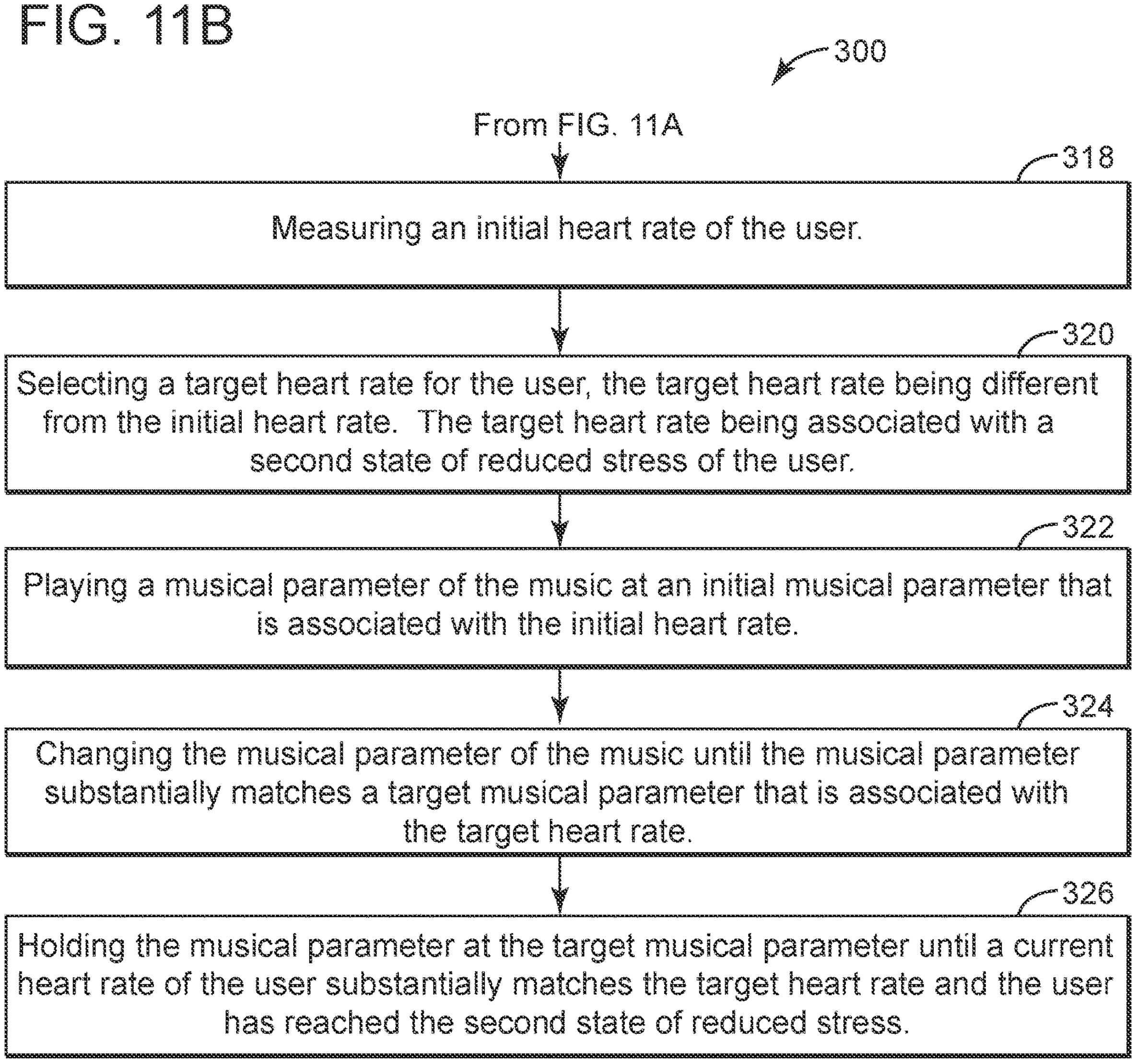
FIG. 11B, depicts an example of a second part of the flow diagram of FIG. 11A of the method of reducing stress by a user of a stress reducing system, in accordance with aspects described herein.

Referring more specifically to FIG. 11B, an example is depicted of a second part of the flow diagram 300 of the method of reducing stress by a user of a stress reducing system 100, in accordance with aspects described herein. The portion of the flow diagram 300 illustrated in FIG. 11B depicts optional examples of the method colloquially named the Focus Feature method.

At 318, an initial heart rate of the user may be measured with the heart rate sensor 128.

At 320, a target heart rate for the user is selected, the target heart rate being different from the initial heart rate. The target heart rate being associated with a second state of reduced stress of the user.

At 322, a musical parameter of the music is played at an initial musical parameter that is associated with the first initial heart rate. The musical parameter can be, for example, tempo or volume, if the music is played as an audio. Alternatively, the musical parameter can be, for example, intensity or frequency, if the music is played via the vibrators. Additionally, the musical parameter can be any one or any combination of parameters, such as tempo, volume, frequency or intensity.

At 324, the musical parameter of the music is gradually changed until the musical parameter substantially matches a target musical parameter that is associated with the target heart rate.

At 326, the musical parameter may be held at the target musical parameter until a current heart rate of the user substantially matches the target heart rate and the user has reached the second state of reduced stress.

Feel Feature

A Third Example Stress Reduction Technique

As an overview, a user will select a musical piece, such as a song, from the App 106 or other device to hear and feel. The vibrators 124, 125A-B, 144 and 145A-B in the first-hand and second-hand wrist devices 102, 104 may match a musical parameter of the musical piece. For example, the vibrators may match a selected song's pitch by associating the vibration frequency to the pitch. A lower pitch may be associated with a lower frequency vibration and a higher pitch may be associated with a higher frequency vibration. One vibrator (for example 124, 144) on each wrist device 102, 104 may be assigned to a lower frequency range. Another vibrator (for example 125A, 145A) on each wrist device 102, 104 may be assigned to a mid-range frequency. The other vibrator (for example 125B 145B) on each wrist device 102, 104 may be assigned to a higher range frequency. This enables the user to feel the entire song, since music typically has more than one instrument playing different pitches at the same time.

The vibrators 124, 125A-B, 144, 145A-B in each wrist device 102, 104 may also match the songs volume by associating the vibration intensity levels to the songs volume. A lower volume sound may be matched with a lower intensity vibration and a higher volume sound may be matched with a higher intensity vibration.

The music volume may gradually and steadily be decreased by the system 100 to help the user reach a more calm and relaxed state at a determined lower target heart rate. The system 100 will assess/measure the users heart rate with heart rate sensor 128 to determine how long to continue the rate of gradually fading out the song and vibrations. If the user is using this "Feel Feature" technique to go to sleep, the target heart rate may be lower than if the user were using it while awake.

If the user is feeling sluggish, this entire technique may be implemented in the exact opposite direction. For example, the users heart rate may be slow and the target heart rate may be set higher than the initial heart rate. The music and vibrations will then be increased instead of decreased.

Figure 12:
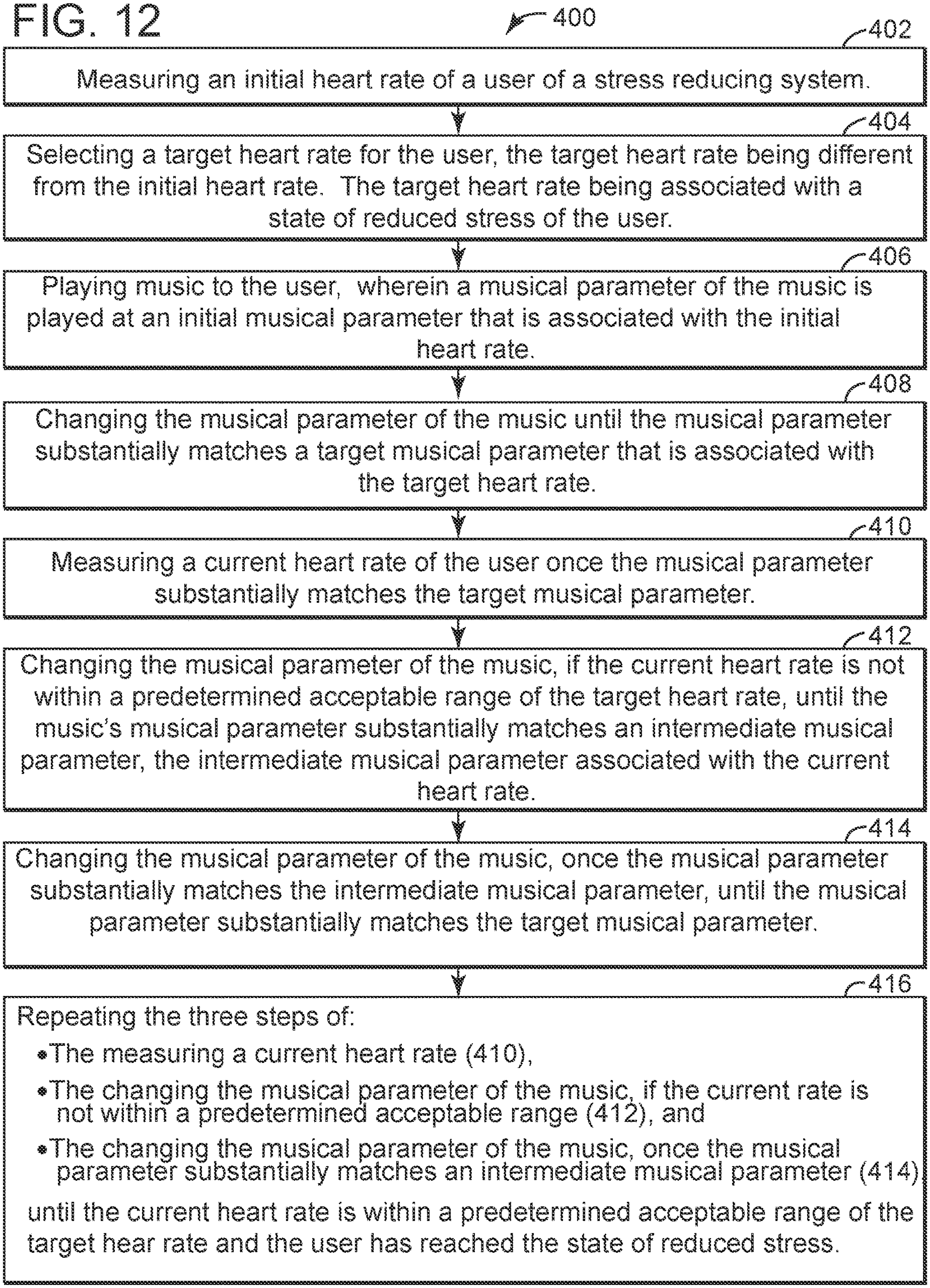
FIG. 12, depicts another example of a flow diagram of a method of reducing stress by a user of a stress reducing system 100, in accordance with aspects described herein.

Referring more specifically to FIG. 12, an example is depicted of a flow diagram 400 of a method of reducing stress by a user of a stress reducing system 100, in accordance with aspects described herein. The flow diagram 400 depicts examples of the method colloquially named the Feel Feature method.

The method 400 begins at 402, wherein an initial heart rate of a user of a stress reducing system is measured. This may be done with heartrate sensor 128.

At 404, a target heart rate is selected for the user, the target heart rate being different from the initial heart rate. The target heart rate being associated with a state of reduced stress of the user.

At 406, music is played to the user, wherein a musical parameter of the music is played at an initial musical parameter that is associated with the first initial heart rate. The musical parameter may be a tempo, a volume, a frequency and/or an intensity. The system 100 may play the music, for example, as an audio of selected music. Additionally, the vibrators 124, 125A-B, 144, 145A-B may play the music as musical beats associated with the music that are felt by the user. The musical beats played by the vibrators may simulate a feel to the user associated with playing the music with one or more percussion instruments.

At 408, the musical parameter of the music is changed until the musical parameter substantially matches a target musical parameter that is associated with the target heart rate.

At 410, a current heart rate of the user is measured once the musical parameter substantially matches the target musical parameter.

At 412, the musical parameter of the music is changed, if the current heart rate is not within a predetermined acceptable range of the target heart rate, until the music's musical parameter substantially matches an intermediate musical parameter. The intermediate musical parameter is associated with the current heart rate.

At 414, the musical parameter of the music is changed, once the musical parameter substantially matches the intermediate musical parameter, until the musical parameter substantially matches the target musical parameter.

At 416, three steps of:

The measuring a current heart rate (step 410), The changing the musical parameter of the music, if the current heart rate is not within a predetermined acceptable range (step 412), and The changing the musical parameter of the music, once the musical parameter substantially matches an intermediate musical parameter (step 414), until the current heart rate is within a predetermined acceptable range of the target heart rate and the user has reached the state of reduced stress.

Figure 13:
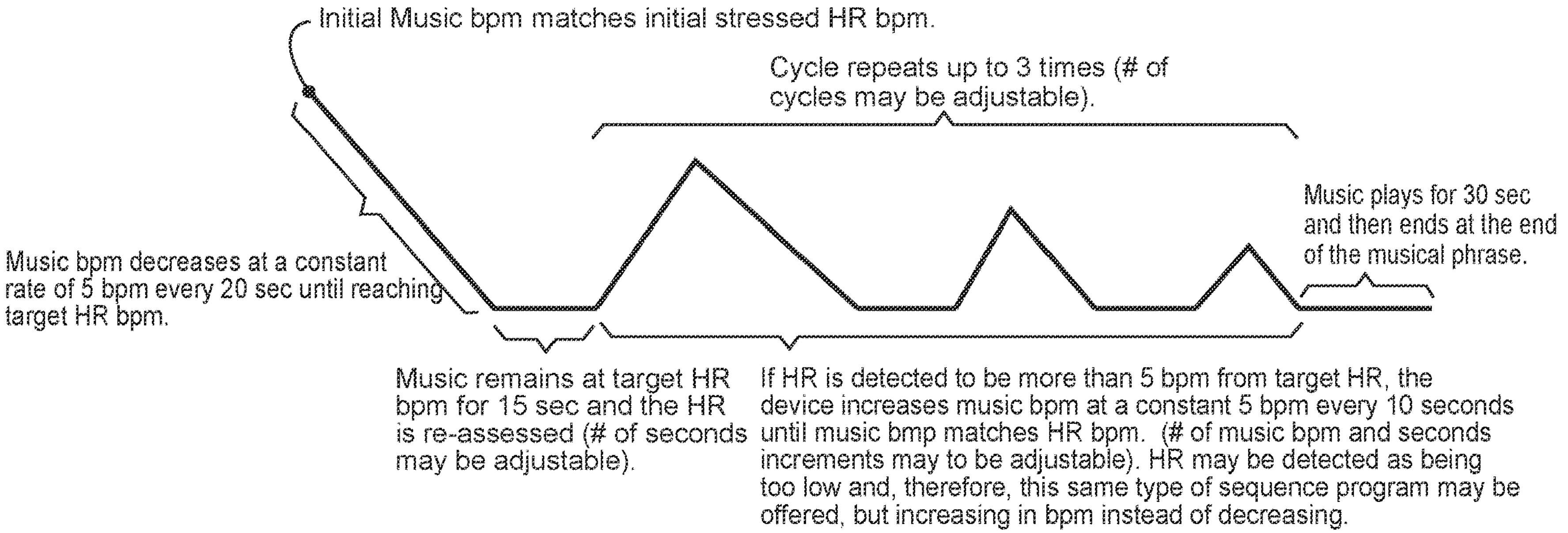
FIG. 13, depicts another example of a graphical representation of a "Feel Feature" stress reduction technique performed by the system of FIG. 1 in accordance with aspects described herein.

Referring to FIG. 13, another example is depicted of a graphical representation of a "Feel Feature" stress reduction technique performed by the system of FIG. 1 in accordance with aspects described herein. In this case, the musical parameter is tempo (i.e., beats per minute).

Figure 14:
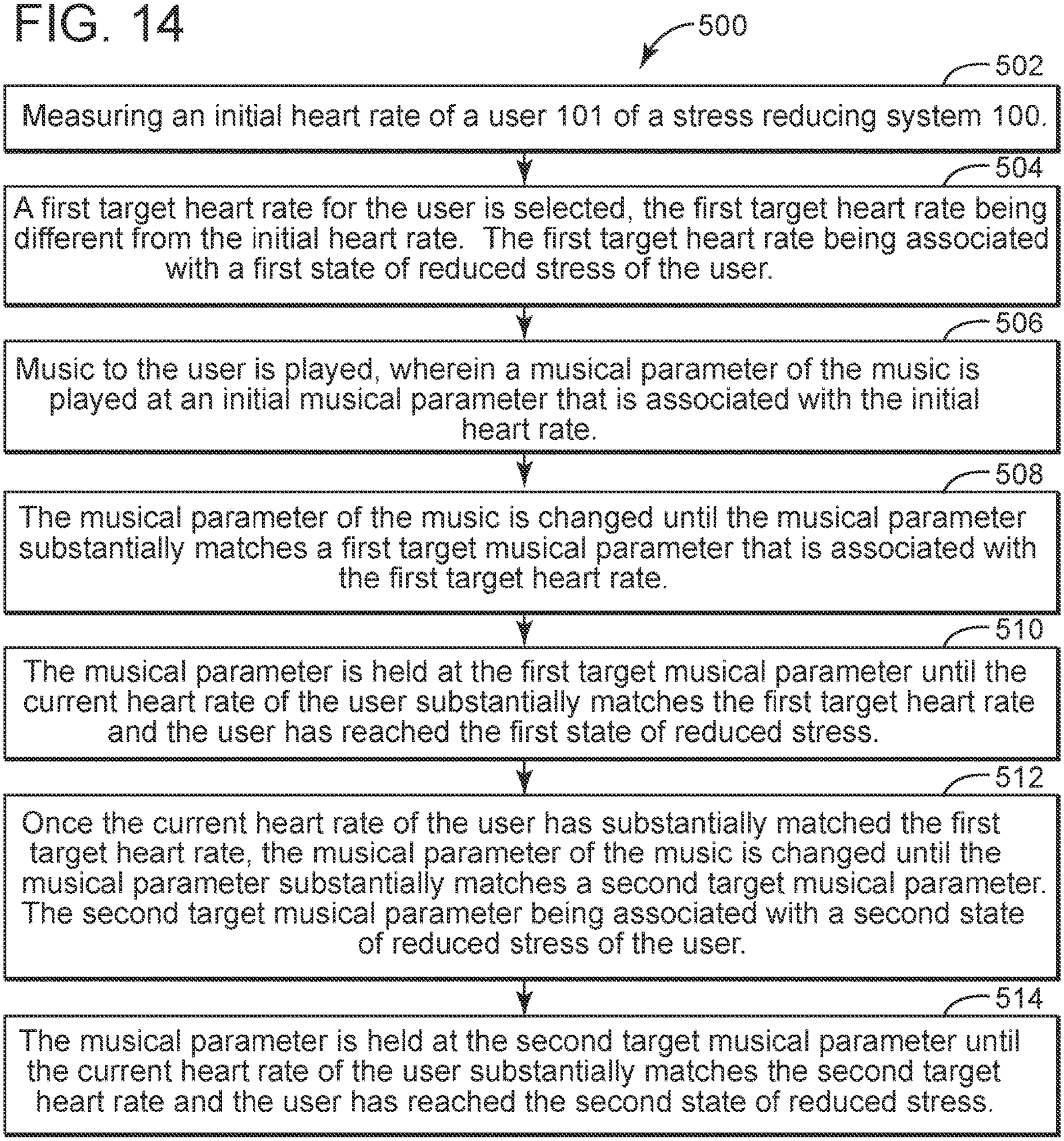
FIG. 14, depicts another example of a flow diagram of a method of reducing stress by a user of a stress reducing system, in accordance with aspects described herein.

Referring to FIG. 14, an example is depicted of a flow diagram 500 of a method of reducing stress by a user of a stress reducing system 100, in accordance with aspects described herein. The flow diagram 500 depicts examples of the method colloquially named the Feel Feature method.

The method 500 begins at 502, wherein an initial heart rate of a user 101 of a stress reducing system 100 is measured.

At 504, a first target heart rate for the user is selected, the first target heart rate being different from the initial heart rate. The first target heart rate being associated with a first state of reduced stress of the user.

At 506, music to the user is played, wherein a musical parameter of the music is played at an initial musical parameter that is associated with the initial heart rate. The musical parameter may be a tempo, a volume, a frequency and/or an intensity. The system 100 may play the music, for example, as an audio of selected music. Additionally, the vibrators 124, 125A-B, 144, 145A-B may play the music as musical beats associated with the music that are felt by the user. The musical beats played by the vibrators may simulate a feel to the user associated with playing the music with one or more percussion instruments.

At 508, the musical parameter of the music is changed until the musical parameter substantially matches a first target musical parameter that is associated with the first target heart rate.

At 510, the musical parameter is held at the first target musical parameter until the current heart rate of the user substantially matches the first target heart rate and the user has reached the first state of reduced stress.

At 512, once the current heart rate of the user has substantially matched the first target heart rate, the musical parameter of the music is changed until the musical parameter substantially matches a second target musical parameter. The second target musical parameter being associated with a second state of reduced stress of the user.

At 514, the musical parameter is held at the second target musical parameter until the current heart rate of the user substantially matches the second target heart rate and the user has reached the second state of reduced stress.

Figure 15:
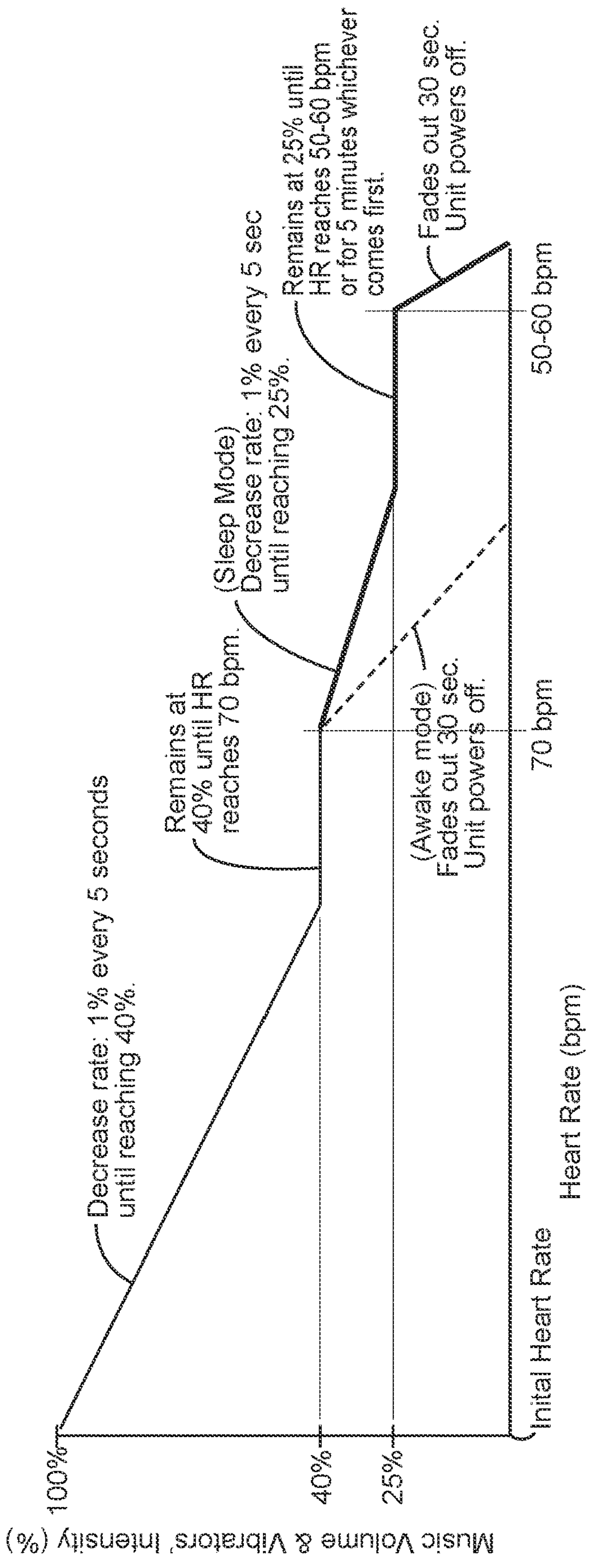
FIG. 15, depicts another example of a graphical representation of a "Feel Feature" stress reduction technique performed by the system of FIG. 1 in accordance with aspects described herein.

Referring to FIG. 15, another example is depicted of a graphical representation of a "Feel Feature" stress reduction technique performed by the system of FIG. 1 in accordance with aspects described herein. In this case, the musical parameter is volume and vibration intensity.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

The invention claimed is:

1. A system for reducing stress of a user, the system comprising:

a first-hand wrist device comprising a first user interface module (first UIM) connected to a first wrist strap:

the first UIM comprising a first vibrator configured to transmit controlled vibrations to a user's first wrist, the controlled vibrations of the first vibrator configured to simulate a feel to the user associated with playing a first portion of a musical piece with a percussion instrument, a first accelerometer mounted on the first UIM, the first accelerometer configured to detect movement of a user's first hand, wherein the first accelerometer is in communication with the first vibrator through the system in a manner that the first vibrator is configured to simulate a feel to the user associated with playing the percussion instrument with the detected movement of the user's first hand, and the first wrist strap being configured to strap the first UIM to the user's first wrists and a second-hand wrist device comprising a second user interface module (second UIM) connected to a second wrist strap:

the second UIM comprising a second vibrator configured to transmit controlled vibrations to a user's second wrist, the controlled vibrations of the second vibrator configured to simulate a feel to the user associated with playing a second portion of the same musical piece with the same percussion instrument, wherein the first portion is different from the second portion, a second accelerometer mounted on the second UIM, the second accelerometer configured to detect movement of a user's second hand, wherein the second accelerometer is in communication with the second vibrator through the system in a manner that the second vibrator is configured to simulate a feel to the user associated with playing the percussion instrument with the detected movement of the user's second hand, and the second wrist strap being configured to strap the second UIM to a user's second wrist;

wherein the first-hand and the second-hand wrist devices are configured to provide a stress alert to the user indicating that the system has detected stress of the user through vibrations induced by the first and the second vibrators respectively, prior to the system applying one or more stress reduction techniques to alleviate the stress.

2. The system of claim 1, comprising:

at least one of a hands occupied control, a hearing occupied control, a sight occupied control and an all senses available control, wherein:

the hands occupied control is mounted on one of the first and second UIM, the hands occupied control configured to signal to the system that the hands of the user are occupied and are not currently available to participate in the one or more stress reduction techniques, the hearing occupied control is mounted on one of the first and second UIM, the hearing occupied control configured to signal to the system that the hearing of the user is occupied and is not currently available to participate in the one or more stress reduction techniques, the sight occupied control is mounted on one of the first and second UIM, the sight occupied control configured to signal to the system that the sight of the user is occupied and is not currently available to participate in the one or more stress reduction techniques, and the all senses available control is mounted on one of the first and second UIM, the all senses available control configured to signal to the system that all of the senses of the user are available to participate in the one or more stress reduction techniques; and wherein the system is configured in a manner that, after providing the stress alert to the user, the system does not apply the one or more stress reduction techniques until receiving at least one signal from the bands occupied control, hearing occupied control sight occupied control or all senses available control.

3. The system of claim 1, comprising:

the first wrist strap comprising one or more first wrist strap vibrators, the one or more first wrist strap vibrators configured to transmit controlled vibrations to the user's first wrist, the controlled vibrations of the one or more first wrist strap vibrators configured to simulate a feel to the user associated with playing the first portion of the same musical piece with the same percussion instrument; and the second wrist strap comprising one or more second wrist strap vibrators, the one or more second wrist strap vibrators configured to transmit controlled vibrations to the user's second wrist, the controlled vibrations of the one or more second wrist strap vibrators configured to simulate a feel to the user associated with playing the second portion of the same musical piece with the same percussion instrument.

4. The system of claim 1, comprising a heart rate sensor mounted on one of the first or second UIM, a heart rate sensor configured to measure the heart rate of the user.

5. The system of claim 1, comprising a software application installed at least on one of the first UIM, the second UIM or a separate computerized device, the software application in communication with the first-hand wrist device and the second-hand wrist device.

* * * * *